(12) United States Patent
Lopez (10) Patent No.: US 10,016,756 B2
(45) Date of Patent: Jul. 10, 2018

(54) DISPOSABLE PIPETTE TIP AND METHODS OF USE

(71) Applicant: Duke University, Durham, NC (US)

(72) Inventor: Gabriel P. Lopez, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 15/466,998

(22) Filed: Mar. 23, 2017

(65) Prior Publication Data

US 2017/0197206 A1 Jul. 13, 2017

Related U.S. Application Data

(63) Continuation of application No. PCT/US2015/052059, filed on Sep. 24, 2015.

(60) Provisional application No. 62/054,445, filed on Sep. 24, 2014.

(51) Int. Cl.
*B01L 3/00* (2006.01)
*B01L 3/02* (2006.01)
*G01N 1/40* (2006.01)

(52) U.S. Cl.
CPC .......... *B01L 3/0275* (2013.01); *G01N 1/4077* (2013.01); *B01L 2300/0858* (2013.01); *B01L 2400/0433* (2013.01); *G01N 2001/4094* (2013.01)

(58) Field of Classification Search
None
See application file for complete search history.

(56) References Cited

U.S. PATENT DOCUMENTS 4,790,183 A * 12/1988 Pfost .................... G01F 23/2966
367/908
4,846,003 A * 7/1989 Marquiss .............. B01L 3/0275
422/931

(Continued)

FOREIGN PATENT DOCUMENTS

WO WO-2008092607 A1 * 8/2008 .............. B01L 3/021

OTHER PUBLICATIONS

Goddard, et al., Analytical Performance of an Ultrasonic Particle Focusing Flow Cytometer; Anal. Chem. (79), 8740-8746 (2007).

(Continued)

*Primary Examiner* — Jill A Warden
*Assistant Examiner* — Brittany I Fisher
(74) *Attorney, Agent, or Firm* — NK Patent Law, PLLC (57) ABSTRACT

A kit for detection of an analyte of interest in a liquid sample, and methods of using, are provided. The kit may include a pipette and a disposable pipette tip configured to engage the pipette. The pipette tip may define an acoustic channel configured for allowing flow-through of a liquid. The kit may also include a vibratory device in communication with the acoustic channel and configured for imparting a vibratory force thereto. The impartation of the vibratory force may create standing acoustic waves, thereby separating any negative acoustic contrast particles (NACPs) from the remaining contents of the liquid sample. The NACPs may capable of biospecific recognition of the analyte of interest, thereby separating the analytes of interest, which can then be collected or analyzed accordingly.

22 Claims, 3 Drawing Sheets

(56) References Cited

U.S. PATENT DOCUMENTS

| | | | |
|---|---|---|---|
| 6,003,388 A * | 12/1999 | Oeftering | B01L 3/0241 422/417 |
| 7,340,957 B2 | 3/2008 | Kaduchak et al. | |
| 2002/0074342 A1* | 6/2002 | Shafer | B01J 19/0046 222/56 |
| 2008/0099572 A1* | 5/2008 | Tollens | A01M 1/205 239/4 |
| 2008/0245709 A1* | 10/2008 | Kaduchak | B01D 21/283 209/599 |
| 2009/0029870 A1* | 1/2009 | Ward | G01N 15/1404 506/9 |
| 2009/0045107 A1 | 2/2009 | Ward et al. | |
| 2009/0078787 A1* | 3/2009 | Xu | B23K 3/0638 239/102.2 |
| 2010/0024529 A1* | 2/2010 | Dillingham | G01N 13/02 73/64.52 |
| 2011/0024335 A1 | 2/2011 | Ward et al. | |
| 2012/0015419 A1* | 1/2012 | Laugharn, Jr. | B01F 11/0283 435/173.7 |
| 2013/0014826 A1 | 1/2013 | Kaduchak et al. | |
| 2013/0153677 A1* | 6/2013 | Leen | B01L 3/0268 239/102.1 |
| 2014/0099240 A1* | 4/2014 | Misono | B01F 13/0025 422/514 |

OTHER PUBLICATIONS

Piyasena, M. E., et al., Multinode Acoustic Focusing for Parallel Flow Cytometry; Analytical Chemistry, 2012(84): 1831-1839.

PCT, International Search Report and Written Opinion for International Patent Application No. PCT/US2015/052059 dated Jan. 5, 2016.

PCT, International Preliminary Report on Patentabililty for International Patent Application No. PCT/US2015/052059 dated Mar. 28, 2017.

\* cited by examiner

DISPOSABLE PIPETTE TIP AND METHODS OF USE

CROSS REFERENCE TO RELATED APPLICATIONS

This application claims the benefit of PCT Patent Application No. PCT/US15/52059 filed Sep. 24, 2015, which claims the benefit of U.S. Provisional Application 62/054,445 filed Sep. 24, 2014, the disclosure of both of which is hereby incorporated by reference in its entirety.

FEDERAL FUNDING LEGEND

The invention was made with Government support under Federal Grant No. DMR-1121107 awarded by the National Science Foundation and under Federal Grant No. 1R21GM111584 awarded by the National Institutes of Health. The Government has certain rights in the invention.

TECHNICAL FIELD

The presently disclosed subject matter relates to disposable pipette tips including a vibrating device, and methods of using. Specifically, the disposable pipette tips may be used for point-of-care assays based on biospecific negative acoustic contrast particles.

BACKGROUND

Techniques to rapidly separate and detect different types of cells and other analytes of interest from biological samples are of interest in scientific research, the biotechnology industry and medicine. For example, fluorescence activated cell sorting (FACS) is now a conventional and standard methodology, but it requires very expensive equipment and is inherently limited by the serial nature of single cell optical sorting.

In another approach, particles within an acoustic channel can be separated from other components in a solution using acoustic force manipulation. See e.g., U.S. Pat. No. 7,340,957 issued Mar. 11, 2008, which is herein incorporated by reference in its entirety. Particles exposed to an ultrasonic standing wave field will experience an average drift force positioning them at local pressure potential minima within an acoustic radiation pressure force potential. See e.g., U.S. Patent Application Publication No. 2008/0245709, published Oct. 9, 2008, which is hereby incorporated by reference in its entirety. The ability of ultrasonic radiation to separate particles derives from the particles' density/compressibility ratio. The density/compressibility contrast between particles and their host medium will determine the positioning of the particles under acoustic radiation exposure. Positive acoustic contrast particles that have a density/compressibility ratio greater than the surrounding medium will be positioned at local pressure potential minima nodes along the center of the focusing chamber (focused). Conversely, negative acoustic contrast particles with a smaller density/compressibility ratio than the surrounding medium will be positioned at local pressure potential minima antinodes along the side of the focusing chamber. After this positioning, positive acoustic contrast particles can be removed from the acoustic focusing chamber, leaving behind only negative acoustic contrast particles which can subsequently be focused to the center of the chamber for analysis.

As described in the '709 patent application publication, most biological particles in aqueous solutions appear to exhibit positive acoustic contrast. Acoustic force manipulation has been used in the past to concentrate (focus) Chinese hamster cells, red blood cells, bacteria, fungal spores, and other types of biological particles in aqueous solution. See the '709 publication as well as Goddard, et al., Analytical Performance of an Ultrasonic Particle Focusing Flow Cytometer; Anal. Chem. (79), 8740-8746 (2007), which is incorporated by reference in its entirety. Exploiting this property, acoustic radiation can be used to trap elastomeric negative acoustic contrast particles (NACPs), and any analytes captured or engaged therewith, or separate them from many biological components within aqueous or unmodified biological samples. While the technology has improved, existing assays still suffer from the need for equipment that is not easily adapted to a point-of-care format.

Accordingly, there remains an unmet need for improved devices and methods for point-of-care assays to detect analytes in biological samples. The present disclosure provides such improved devices and methods.

SUMMARY OF THE DISCLOSURE

According to at least one embodiment of the present disclosure, a kit includes a pipette, a disposable pipette tip configured to engage the pipette, the pipette tip defining an acoustic channel configured for allowing flow-through of a liquid, and a vibratory device in communication with the acoustic channel and configured for imparting a vibratory force thereto.

According to another embodiment, imparting a vibratory force includes creating standing acoustic waves within the acoustic channel.

According to another embodiment, the kit further includes a biospecific negative acoustic contrast particles (NACPs) for separating an analyte of interest.

According to another embodiment, the pipette tip further defines a reservoir for suspending the liquid therein and the reservoir configured for fluid communication with the acoustic channel and positioned between the pipette and the acoustic channel.

According to another embodiment, the vibratory device is housed exterior of the reservoir.

According to another embodiment, the vibratory device is housed within a ring encircling the acoustic channel.

According to another embodiment, the acoustic channel is formed of one or a combination of metal, glass, quartz, or plastic.

According to another embodiment, the vibratory device is a piezoelectric vibrator.

According to another embodiment, the piezoelectric vibrator is a PZT crystal or a quartz crystal.

According to another embodiment, the kit further includes one or a combination of a power supply, waveform generator, or amplifier for providing power to the vibratory device.

According to another embodiment, the pipette includes the one or a combination of power supply, waveform generator or amplifier.

According to another embodiment, a disposable pipette tip defines an acoustic channel and configured for allowing flow-through of a liquid. A vibratory device is in communication with the acoustic channel and configured for imparting a vibratory force thereto.

According to another embodiment, imparting a vibratory force includes creating standing acoustic waves within the acoustic channel.

According to another embodiment, the pipette tip further defines a reservoir for suspending the liquid therein. The reservoir is configured for fluid communication with the acoustic channel and positioned between the pipette and the acoustic channel.

According to another embodiment, the vibratory device is housed exterior of the reservoir.

According to another embodiment, the vibratory device is housed within a ring encircling the acoustic channel.

According to another embodiment, the acoustic channel is formed of one or a combination of metal, glass, quartz, or plastic.

According to another embodiment, the vibratory device is a piezoelectric vibrator.

According to another embodiment, the piezoelectric vibrator is a PZT crystal or a quartz crystal.

According to another embodiment, a method for separating an analyte includes engaging a pipette tip with a pipette. The pipette tip includes an acoustic channel configured for allowing flow-through of a fluid, and a vibratory device in communication with the acoustic channel and configured for imparting a vibratory force thereto. The method includes aspirating a liquid sample to be analyzed for the analyte of interest within the pipette tip using the pipette. The liquid sample includes negative acoustic contrast particles (NACPs) capable of biospecific recognition of the analyte of interest;

According to another embodiment, the method includes imparting a vibratory force to the acoustic channel of the pipette tip by actuating the vibratory device, thereby trapping the NACPs in the pipette tip, ejecting the sample liquid contents through the vibratory force of the acoustic channel, thereby retaining the trapped NACPs capable of biospecific recognition of the analyte of interest within the pipette tip, and aspirating one or more additional fluids within the pipette tip, wherein release of the NACPs into the one or more additional fluids is allowed for upon cessation of actuation of the vibratory device.

According to another embodiment, imparting a vibratory force includes creating standing acoustic waves within the acoustic channel.

According to another embodiment, the liquid sample is a biological sample.

According to another embodiment, the analyte includes an ion, small molecule, antigen, protein, nucleic acid, carbohydrate, virus, cell or biomarker.

According to another embodiment, actuating the vibratory device is performed either prior to or subsequent to aspiration of the liquid sample.

According to another embodiment, the method further includes ejecting the one or more additional fluids either in the presence of the vibratory force. The NACPs are retained in the pipette tip, or in the absence of the vibratory force. The NACPs are released into the additional fluid.

According to another embodiment, the one or more additional fluids include a reagent capable of binding to the analyte of interest to allow for detection of the analyte within or outside of the pipette tip.

According to another embodiment, the reagent includes antibodies, receptors, ligands, nucleic acids, aptamers, synthetic host molecules, enzymes, stains, dyes, or chromophores.

According to another embodiment, the additional fluid includes a reagent capable of binding to the analyte of interest, and the additional fluid is ejected in the absence of the vibratory force to allow for one or both of detection and collection of the analyte outside the pipette tip.

According to another embodiment, the reagent includes antibodies, receptors, ligands, nucleic acids, aptamers, synthetic host molecules, enzymes, stains, dyes, or chromophores.

According to another embodiment, the analyte is detected using a microscope or a flow cytometer.

According to another embodiment, the method includes, in the presence of the vibratory force wherein the NACPs are trapped within the pipette tip, aspirating one or more additional fluid that is a wash fluid within the pipette tip and ejecting the wash fluid. The aspirating the wash fluid may be repeated multiple times.

According to another embodiment, the reagent is an antibody and the method further includes ejecting the additional fluid in the presence of the vibratory force and optionally aspirating and ejecting one or more additional fluid that is a wash fluid in the presence of the vibratory force, aspirating one or more additional fluid includes a secondary antibody in the presence of the vibratory force, and ceasing actuation of the vibratory force. The analyte is detected either within the pipette tip or outside the pipette tip after ejection of the additional fluid that forms the secondary antibody.

According to another embodiment, the NACPs are color-coded for detection.

According to another embodiment, the NACPs are coded to allow for multiplex detection.

According to another embodiment, a kit for detection of an analyte of interest in a liquid sample includes a disposable pipette tip configured to engage a pipette. The pipette tip defines an acoustic channel configured for allowing flow-through of a liquid, and the pipette tip has a vibratory device in communication with the acoustic channel and that is configured for imparting a vibratory force thereto. The kit includes negative acoustic contrast particles (NACPs) capable of biospecific recognition of the analyte of interest.

According to another embodiment, imparting a vibratory force includes creating standing acoustic waves within the acoustic channel.

According to another embodiment, the pipette tip further defines a reservoir for suspending the liquid therein, the reservoir configured for fluid communication with the acoustic channel and positioned between the pipette and the acoustic channel.

According to another embodiment, the vibratory device is housed exterior of the reservoir.

According to another embodiment, the vibratory device is housed within a ring encircling the acoustic channel.

According to another embodiment, the acoustic channel is formed of metal, glass, quartz, and/or plastic.

According to another embodiment, the vibratory device is a piezoelectric vibrator.

According to another embodiment, the piezoelectric vibrator is a PZT crystal or a quartz crystal.

According to another embodiment, the kit further includes one or a combination of a power supply, waveform generator, or amplifier for providing power to the vibratory device for imparting the vibratory force.

According to another embodiment, the pipette tip includes one or a combination of the power supply, waveform generator or amplifier.

According to another embodiment, the liquid sample is a biological sample.

According to another embodiment, the analyte includes an ion, small molecule, antigen, protein, nucleic acid, carbohydrate, virus, cell or biomarker.

According to another embodiment, the kit includes one or more reagents capable of binding to the analyte of interest to allow for detection of the analyte within or outside of the pipette tip.

According to another embodiment, one or more reagents include one or a combination of antibodies, receptors, ligands, nucleic acids, aptamers, synthetic host molecules, enzymes, stains, dyes, or chromophores.

According to another embodiment, a vibratory device is configured for being engageable with one of a pipette or a disposable pipe tip and is further configured for imparting vibratory forces to an acoustic channel extending from the disposable pipette tip. A liquid including a biological sample that contains negative acoustic contrast particles (NACPs) is aspirated into the acoustic channel for interacting with the vibratory forces.

According to another embodiment, the vibratory device is housed exterior of a reservoir defined within the pipette tip.

According to another embodiment, the vibratory device defines a ring shape that encircles the acoustic channel when engaged therewith.

According to another embodiment, the vibratory device is a piezoelectric vibrator.

According to another embodiment, the piezoelectric vibrator is a PZT crystal or a quartz crystal.

According to another embodiment, the device is further in communication with one or a combination of a power supply, waveform generator, or amplifier for providing power to the vibratory device for imparting the vibratory force.

BRIEF DESCRIPTION OF THE DRAWINGS

The foregoing aspects and other features of the disclosure are explained in the following description, taken in connection with the accompanying drawings, wherein.

DETAILED DESCRIPTION OF THE DISCLOSURE

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs.

Figure 1A:
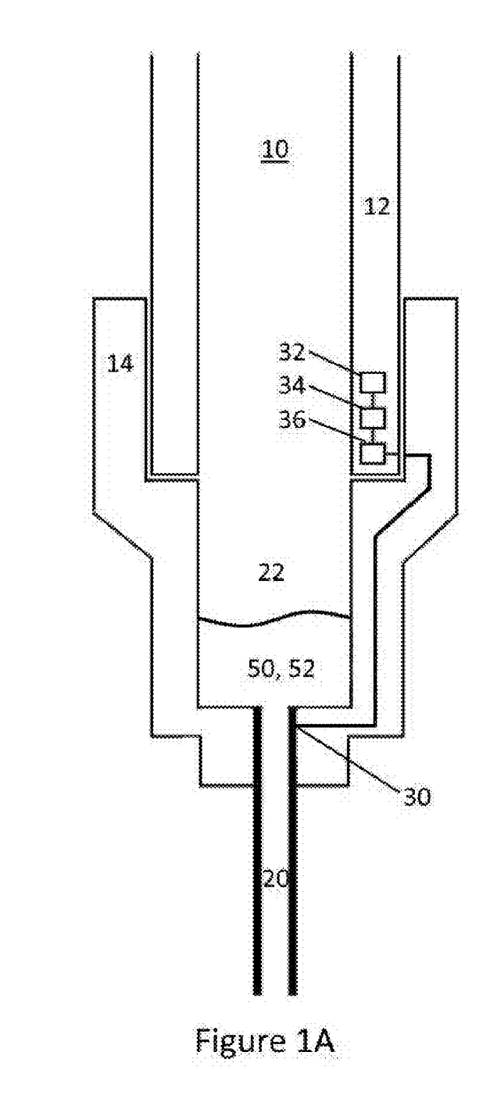
FIG. 1A is a side view of a kit including a pipette and a disposable pipette tip according to at least one embodiment of the present disclosure.
Figure 1B:
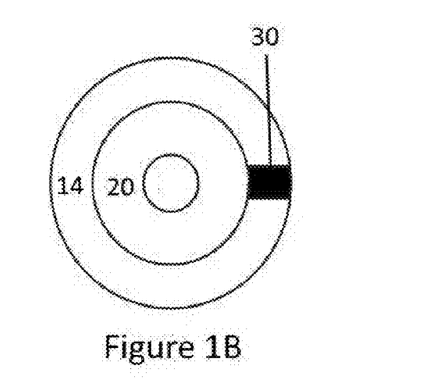
FIG. 1B is a top view of a kit including a pipette tip, acoustic channel and vibratory device according to at least one embodiment of the present disclosure.
Figure 1C:
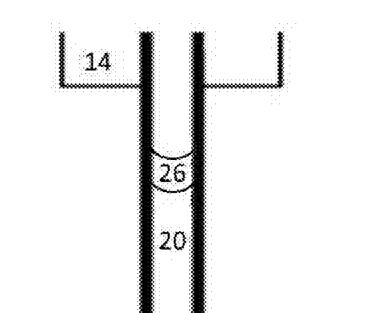
FIG. 1C is a view of a kit including an acoustic channel, pipette tip and a ring according to at least one embodiment of the present disclosure.

FIG. 1 depicts a kit 10 comprising a pipette 12, a pipette tip 14 and a vibratory device 30 according to at least one embodiment of the present invention. The kit 10, and methods described herein, may be used for point-of-care assays based on biospecific negative acoustic contrast particles (NACPs) 40. Specifically, the kit 10 may be used for detection of an analyte of interest in a liquid sample 50. The liquid sample may be a biological sample. The analyte may comprise an ion, small molecule, antigen, protein, nucleic acid, carbohydrate, virus, cell or biomarker. The term "biospecific negative acoustic contrast particle (NACP)" refers to a negative acoustic contrast particle that includes a biomolecule capable of binding to an analyte of interest in a liquid sample, an analyte such as an ion, small molecule, antigen, protein, nucleic acid, carbohydrate, virus, cell or biomarker. The biomolecule can be one or a combination of a ligand, a receptor, an aptamer, a peptide, a protein, an antibody, or a nucleic acid.

According to at least one embodiment, the kit 10 may include biospecific negative acoustic contrast particles (NACPs) 40. The NACPs may be capable of biospecific recognition of the analyte of interest, and, as described more fully infra, biospecific NACPs 40 may be included for separating the analyte of interest. The NACPs may be added to the liquid sample 50 for detection of the analyte of interest within the sample. The liquid sample 50 may be a biological sample.

According to one or more embodiments, the pipette tip 14 is disposable. The pipette tip may be configured to engage the pipette 12. As one skilled in the art would appreciate, engagement of the pipette tip 14 with the pipette 12 may be accomplished using a number of structures and/or mechanisms well known in the art. The tip 14 may define an acoustic channel 20 configured for allowing flow-through of a liquid. The acoustic channel 20 may be comprised of one or a combination of metal, glass, quartz, or plastic. The acoustic channel 20 may be of a uniform width or diameter in order to support an standing acoustic wave 2 (i.e., a acousticfluidic channel). Alternatively, the acoustic channel 20 may include at least a portion having a uniform width or diameter configured to support a standing acoustic wave 2.

Further, the pipette tip 14 may define a reservoir 22 for suspending the liquid therein, the reservoir 22 configured for fluid communication with the acoustic channel 20 and positioned between the pipette 12 and the acoustic channel 20.

According to some embodiments, the vibratory device 30 may be in communication with the acoustic channel 20. In some embodiments, the vibratory device 30 may be configured for being engageable with either a pipette 12 or a disposable pipette tip 14. In some embodiments, the vibratory device 30 may be housed exterior of the reservoir 22, within or exterior to the pipette tip 14. In another embodiment, the vibratory device 30 may be housed within a ring 26 encircling the acoustic channel 20. In yet another embodiment, the vibratory device 30 may be housed within the acoustic channel 20 itself. Further, the vibratory device 30 may be configured for imparting vibratory forces 1 to an acoustic channel 20, wherein the acoustic channel may be extending from the disposable pipette tip 14. A liquid including a biological sample that contains biospecific negative acoustic contrast particles (NACPs) 40 may be aspirated into the acoustic channel 20 for interacting with the vibratory forces 1.

The vibratory device 30 may be a piezoelectric vibrator. The piezoelectric vibrator may be a PZT crystal or a quartz crystal, for example. As one skilled in the art would appreciate, the vibratory device 30 may be coupled to, or in wireless or electronic communication with, one or a combination of a power supply 32, waveform generator 34 or amplifier 36. As depicted in FIG. 1, the power supply 32, waveform generator 34 and/or amplifier 36 may be included in the kit 10 and/or pipette 12 for providing power to the vibratory device 30. Alternatively these components 32, 34, 36 may be included in the pipette tip 14, the ring 26, or some other external device configured for electrical connection with the vibratory device 30. In embodiments where the components 32, 34, 36 are included in the pipette and the According to at least one embodiment, the vibratory device 30 may impart vibratory forces 1, which may include creating standing acoustic waves 2 within the acoustic channel 20. As will be explained in more detail supra, the creating of acoustic standing waves 2 within the acoustic channel 20 permits the separation of negative acoustic contrast particles (NACPs) 40 from positive acoustic contrast particles (PACPs) 42. In biological samples, for example, such separation permits biospecific NACPs 40 to separate from biological cells 42 and other PACP biological matter 42, thereby permitting biospecific analytes to be separated along with the NACPs 40.

The vibratory device 30 of the present disclosure may be positioned in operable communication with the acoustic channel 20, the vibratory device 30, through production of vibratory forces 1, being capable of producing an acoustic standing wave 1 across the channel 20 such that substantially all of the objects in the fluid composition are focused and constrained to a predetermined region (e.g., the central axis of the channel) within the channel 20. The vibratory device may be any device that is capable of generating an acoustic wave 1 across the channel 20. In some embodiments, the vibratory device 30 comprises a piezoelectric transducer. In certain embodiments, the vibratory device 30 comprises a lead zirconate titanate-PZT. In other embodiments, the vibratory device 30 comprises a surface acoustic wave substrate (SAW). In certain embodiments, the SAW comprises a piezoelectric substrate and an interdigitated electrode (IDE). In some embodiments, the vibratory device 30 is bonded to a substrate. The vibratory device 30 generates an acoustic wave across the channel 20 that rapidly and efficiently focuses the objects (e.g., cells, NACPs 40, PACPs 42) to a specific region within the channel. In some embodiments, the objects are focused and constrained along the central axis of the channel 20, however, it is within the scope of the present disclosure that the objects can be focused and constrained anywhere within the channel 20. In some embodiments, the wavelength of the acoustic wave 1 is ½ the width of the channel 20. More information relating to acoustic standing waves 2, and the interactions of PACPs 42 and NACPs 40 therewith can be found in "Elastomeric Negative Acoustic Contrast Particles for Capture, Acoustophoretic Transport, and Confinement of Cells in Microfluidic Systems", published at Langmuir, 2014, 30(14), pp 3923-3927 on Mar. 31, 2014 by the inventor Gabriel Lopez, et al, which is incorporated by reference herein in their entirety. Also see, e.g., M. E. Piyasena, et al. Multinode Acoustic Focusing for Parallel Flow Cytometry. Analytical Chemistry, 2012(84): 1831-1839, which is herein incorporated by reference in its entirety.

According to some embodiments of the present invention, the kit 10 may further include one or more reagents capable of binding to the analyte of interest to allow for detection of the analyte within or outside of the pipette 12 or pipette tip 14. The one or more reagents may include one or a combination of antibodies, receptors, ligands, nucleic acids, aptamers, synthetic host molecules, enzymes, stains, dyes, or chromophores.

According to at least one embodiment, a method for separating an analyte is provided. The method may include providing a pipette 12 and pipette tip 14 according to any of the embodiments described herein, and engaging the pipette tip 14 with the pipette 12. For example, the pipette tip 14 may comprise an acoustic channel 20 configured for allowing flow-through of a fluid, and a vibratory device 30 in communication with the acoustic channel 20 and configured for imparting a vibratory force 1 thereto.

Figure 2:
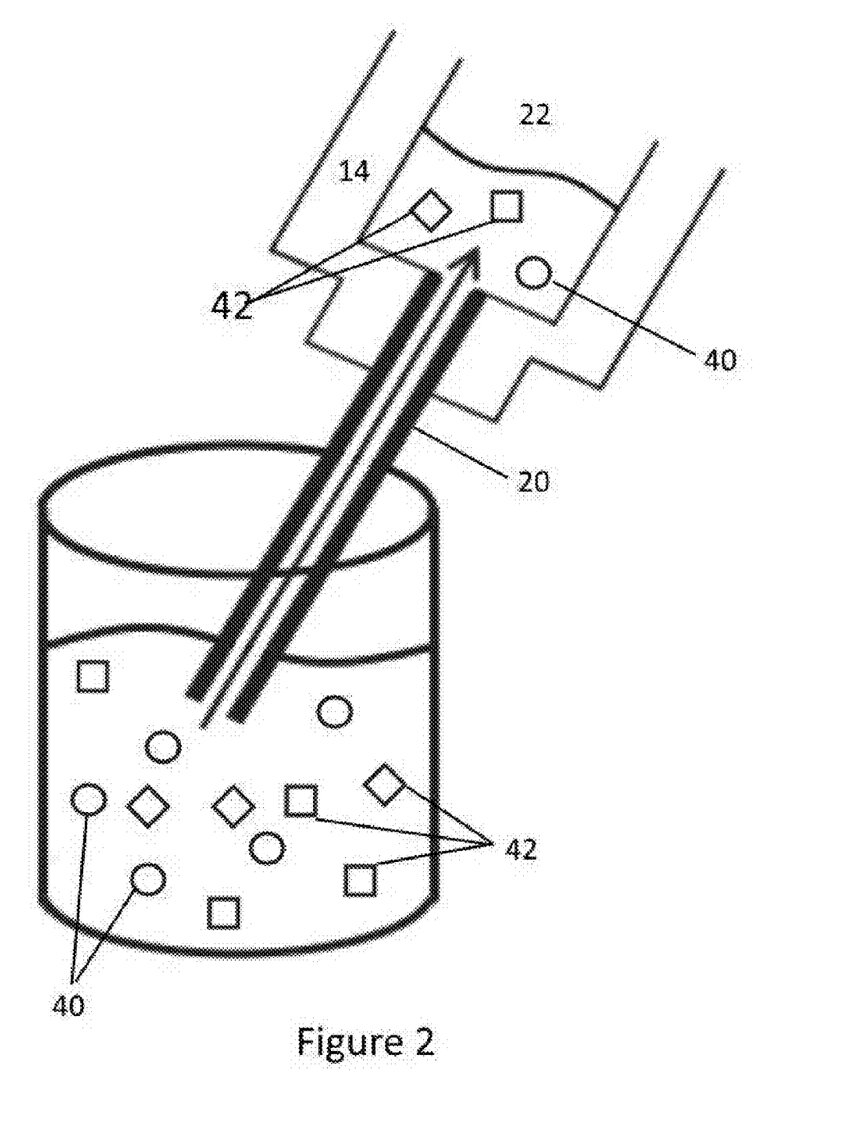
FIG. 2 depicts the aspiration of a liquid within a pipette tip according to at least one embodiment of the present disclosure.
Figure 3A:
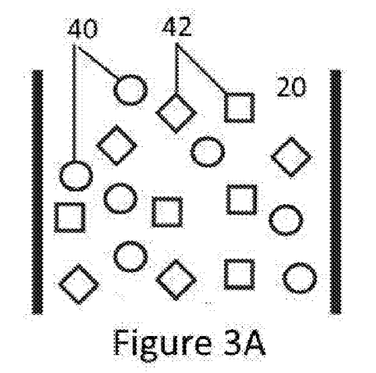
FIG. 3A is a view of the liquid within an acoustic channel with no vibratory force present according to at least one embodiment of the present disclosure.
Figure 3B:
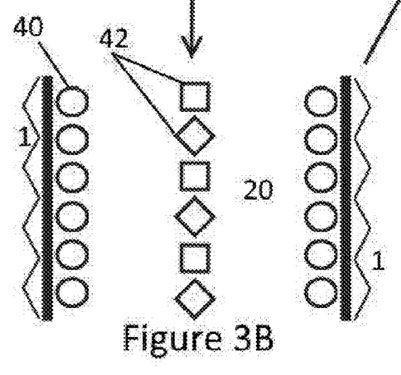
FIG. 3B is a view of the liquid within an acoustic channel in the presence of a vibratory force according to at least one embodiment of the present disclosure.

Referring to FIG. 2, the method includes aspirating a liquid sample 50 to be analyzed for the analyte of interest within the pipette tip 14 using the pipette 12. The liquid sample 50 includes negative acoustic contrast particles (NACPs) 40 capable of biospecific recognition of the analyte of interest. As depicted in FIG. 3A, the NACPs 40 and PACPs 42 are dispersed within the acoustic channel 20 in the absence of the vibratory force 1. The method includes imparting a vibratory force 1 to the acoustic channel 20 of the pipette tip 14 by actuating the vibratory device 30, thereby trapping the NACPs 40 in the pipette tip 14, as depicted in FIG. 3B.

Various processes may be performed on the liquid sample 50 prior to aspirating the liquid sample 50 to be analyzed. Examples of these processes may include target labeling, cell lysis, and depletion. Lysis may involve breaking cell membranes or cell walls to release cell components (organelles, biomolecules, etc.) into the liquid sample 50. Depletion can involve removing a particular component or components in a sample prior to separation. An example of depletion is removal of erythrocytes from a sample by acoustic or other means.

Figure 3C:
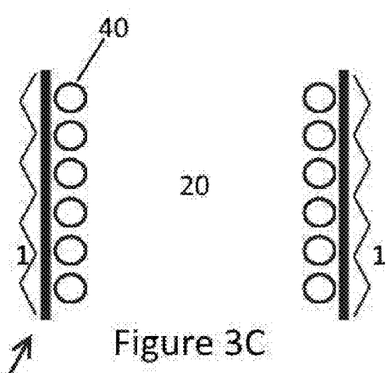
FIG. 3C is a view of the liquid within an acoustic channel following ejection in the presence of a vibratory force according to at least one embodiment of the present disclosure.

Referring to FIG. 3C, the method may further include ejecting the liquid sample 50 through the vibratory force 1 of the acoustic channel 20, thereby retaining the trapped NACPs 40 capable of biospecific recognition of the analyte of interest within the pipette tip 14. By ejecting the liquid sample 50, much of the PACPs 42 originally comprised within the liquid sample 50, such as cells, for example, in the case of a blood sample, have been removed from the pipette tip 14, leaving a larger percentage of NACPs 40 trapped in the tip 14, along with any analyte of interest that may have been captured or retained by the NACPs. In effect, the analyte of interest has been largely separated from much of the remaining liquid sample 50 contents.

According to some embodiments, the method may further include aspirating one or more additional fluids 52 within the pipette tip 14, wherein release of the NACPs 40 into the one or more additional fluids 52 is allowed for upon cessation of actuation of the vibratory device 30. Aspiration may occur in a similar manner as the aspiration depicted in FIG.

2. Aspiration of the additional fluids 52 allows for ejection of trapped NACPs 40 from within the acoustic channel 20 or pipette tip 14.

In some embodiments of the method, the step of actuating the vibratory device 30 may be performed either prior to or subsequent to the step of aspirating the liquid sample 50. For example, the vibratory device 30 may be actuated before aspiration of the liquid sample 50, such that the NACPs 40 of the liquid sample 50 are trapped as they flow through the vibratory forces 1 within the acoustic channel 20. Alternatively, the vibratory device 30 may be actuated subsequent to the aspiration of the liquid sample 50, such that the NACPs 40 of the liquid sample 50 positioned within the vibratory forces 1 of the acoustic channel 20, and may be trapped when ejected through the vibratory forces 1 of the acoustic channel 20.

Figure 3D:
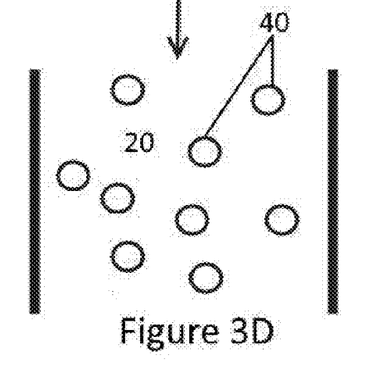
FIG. 3D is a view of the liquid within an acoustic channel with no vibratory force following an ejection through the presence of a vibratory force according to at least one embodiment of the present disclosure.

In one or more embodiments, the method may further include ejecting the one or more additional fluids 52 either in the presence of the vibratory force 1, wherein the NACPs 40 may be retained in the pipette tip 14, or in the absence of the vibratory force 14, wherein the NACPs 40 may be released into the additional fluid 52. FIG. 3D depicts the acoustic channel 20 including NACPs 40 following ejection of the additional fluids 52 in the presence of the vibratory force 1.

In some embodiments, the one or more additional fluids 52 may include a reagent capable of binding to the analyte of interest to allow for detection of the analyte within or outside of the pipette tip 14. The reagent may include antibodies, receptors, ligands, nucleic acids, aptamers, synthetic host molecules, enzymes, stains, dyes, or chromophores.

In other embodiments, the additional fluid 52 may comprise a reagent capable of binding to the analyte of interest, and the additional fluid 52 may be ejected in the absence of the vibratory force 1 to allow for one or both of detection and collection of the analyte outside the pipette tip 14. Again, the reagent may include antibodies, receptors, ligands, nucleic acids, aptamers, synthetic host molecules, enzymes, stains, dyes, or chromophores.

Alternatively, in some embodiments, the reagent is an antibody and the method may further include ejecting the additional fluid 52 that included the antibody in the presence of the vibratory force 1 and optionally aspirating and ejecting one or more additional fluid that is a wash fluid in the presence of the vibratory force 1. In this manner, the unbound antibody may be removed. The method may further include aspirating one or more additional fluid comprising a secondary antibody in the presence of the vibratory force 1. Additionally, the method may further include ceasing actuation of the vibratory force 1, wherein the analyte is detected either within the pipette tip 14 or outside the pipette tip 14 after ejection of the additional fluid comprising the secondary antibody.

In other embodiments, the method may further include, in the presence of the vibratory force 1, wherein the NACPs 40 are trapped within the pipette tip 14, aspirating one or more additional fluid that is a wash fluid within the pipette tip 14 and ejecting the wash fluid, wherein the aspirating the wash fluid may be repeated multiple times.

In at least one embodiment, the analyte may be detected using a microscope or flow cytometer. Further, the NACPs 40 may be color-coded for detection. Alternatively, the NACPs 40 may be coded to allow for multiplex detection. Various analytical techniques may be used to detect the NACPs 40 and/or the analyte of interest including, for example, but not limited to flourometric analysis, colormetric analysis, and image analysis.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods described herein are presently representative of preferred embodiments, are exemplary, and are not intended as limitations on the scope of the invention. Changes therein and other uses will occur to those skilled in the art which are encompassed within the spirit of the invention as defined by the scope of the claims.

The invention claimed is:

1. A kit comprising:
a pipette; and
a disposable pipette tip configured to engage the pipette, the pipette tip defining an acoustic channel configured for allowing flow-through of a liquid, and having a vibratory device in communication with the acoustic channel and configured for imparting a vibratory force thereto, wherein the vibratory device is housed within a ring encircling the acoustic channel.

2. The kit of claim 1, wherein imparting a vibratory force includes creating standing acoustic waves within the acoustic channel.

3. The kit of claim 1, further comprising biospecific negative acoustic contrast particles (NACPs) for separating an analyte of interest.

4. The kit of claim 1, wherein the pipette tip further defines a reservoir for suspending the liquid therein, the reservoir configured for fluid communication with the acoustic channel and positioned between the pipette and the acoustic channel.

5. The kit of claim 1, wherein the vibratory device is a piezoelectric vibrator.

6. The kit of claim 1, wherein the pipette includes one or a combination of power supply, waveform generator or amplifier.

7. A disposable pipette tip defining an acoustic channel configured for allowing flow-through of a liquid, and having a vibratory device in communication with the acoustic channel and configured for imparting a vibratory force thereto, wherein the vibratory device is housed within a ring encircling the acoustic channel.

8. The disposable pipette tip of claim 7, wherein the pipette tip further defines a reservoir for suspending the liquid therein, the reservoir configured for fluid communication with the acoustic channel and positioned between a pipette and the acoustic channel.

9. The disposable pipette tip of claim 7, wherein the vibratory device is a piezoelectric vibrator.

10. A method for separating an analyte comprising:
engaging a pipette tip with a pipette, wherein the pipette tip comprises:
an acoustic channel configured for allowing flow-through of a fluid; and
a vibratory device in communication with the acoustic channel and configured for imparting a vibratory force thereto;
aspirating a liquid sample to be analyzed for an analyte of interest within the pipette tip using the pipette, wherein the liquid sample includes negative acoustic contrast particles (NACPs) capable of biospecific recognition of the analyte of interest;

imparting a vibratory force to the acoustic channel of the pipette tip by actuating the vibratory device, thereby trapping the NACPs in the pipette tip;

ejecting the sample liquid contents through the vibratory force of the acoustic channel, thereby retaining the trapped NACPs capable of biospecific recognition of the analyte of interest within the pipette tip; and aspirating one or more additional fluids within the pipette tip, wherein release of the NACPs into the one or more additional fluids occurs upon cessation of actuation of the vibratory device.

11. The method of claim 10, wherein imparting a vibratory force includes creating standing acoustic waves within the acoustic channel.

12. The method of claim 10, wherein the liquid sample is a biological sample.

13. The method of claim 10, wherein the analyte comprises an ion, small molecule, antigen, protein, nucleic acid, carbohydrate, virus, cell or biomarker.

14. The method of claim 10, further comprising ejecting the one or more additional fluids either in the presence of the vibratory force, wherein the NACPs are retained in the pipette tip, or in the absence of the vibratory force, wherein the NACPs are released into the one or more additional fluids.

15. The method of claim 10, wherein the one or more additional fluids comprises a reagent capable of binding to the analyte of interest to allow for detection of the analyte within or outside of the pipette tip.

16. The method of claim 15, wherein the reagent comprises antibodies, receptors, ligands, nucleic acids, aptamers, synthetic host molecules, enzymes, stains, dyes, or chromophores.

17. The method of claim 10, wherein the one or more additional fluids comprise a reagent capable of binding to the analyte of interest, and the one or more additional fluids are ejected in the absence of the vibratory force to allow for one or both of detection and collection of the analyte outside the pipette tip.

18. The method of claim 17, wherein the reagent comprises antibodies, receptors, ligands, nucleic acids, aptamers, synthetic host molecules, enzymes, stains, dyes, or chromophores.

19. The method of claim 17, wherein the reagent is an antibody and the method further comprising:

ejecting the one or more additional fluids in the presence of the vibratory force and optionally aspirating and ejecting the one or more additional fluids that are a wash fluid in the presence of the vibratory force;

aspirating one or more additional fluid comprising a secondary antibody in the presence of the vibratory force; and ceasing actuation of the vibratory force, wherein the analyte is detected either within the pipette tip or outside the pipette tip after ejection of the additional fluid comprising the secondary antibody.

20. The method of claim 10, further comprising, in the presence of the vibratory force wherein the NACPs are trapped within the pipette tip, aspirating one or more additional fluid that is a wash fluid within the pipette tip and ejecting the wash fluid, wherein the aspirating the wash fluid may be repeated multiple times.

21. The method of claim 10, wherein the NACPs are color-coded for detection.

22. The method of claim 10, wherein the NACPs are coded to allow for multiplex detection.

* * * * *